(12) United States Patent
Volokh et al.

(10) Patent No.: US 8,841,619 B2
(45) Date of Patent: Sep. 23, 2014

(54) METHODS AND SYSTEMS FOR POSITIONING DETECTORS FOR NUCLEAR MEDICINE IMAGING

(75) Inventors: Lana Volokh, Haifa (IL); Nati Herman, Yifat (IL); Roee Khen, Haifa (IL)

(73) Assignee: General Electric Company, Schenectady, NY (US)

(*) Notice: Subject to any disclaimer, the term of this patent is extended or adjusted under 35 U.S.C. 154(b) by 244 days.

(21) Appl. No.: 13/487,043

(22) Filed: Jun. 1, 2012

(65) Prior Publication Data
US 2013/0320234 A1 Dec. 5, 2013

(51) Int. Cl.
*G01T 7/00* (2006.01)
(52) U.S. Cl.
USPC .................................................. 250/363.05
(58) Field of Classification Search
CPC ................................ A61B 6/04; A61B 6/0478
USPC ........................................ 250/363.05, 363.08
See application file for complete search history.

(56) References Cited

U.S. PATENT DOCUMENTS

| | | | |
|---|---|---|---|
| 3,670,163 A * | 6/1972 | Lajus | 378/179 |
| 6,444,987 B1 * | 9/2002 | Treillet et al. | 250/363.05 |
| 7,399,973 B2 | 7/2008 | Stark | |
| 7,456,407 B2 | 11/2008 | Stark | |
| 7,825,383 B2 | 11/2010 | Vija et al. | |
| 2004/0176676 A1 | 9/2004 | Graw | |
| 2004/0262525 A1 * | 12/2004 | Yunker et al. | 250/363.08 |
| 2010/0205740 A1 | 8/2010 | Tybinkowski et al. | |
| 2011/0026685 A1 | 2/2011 | Zilberstein et al. | |

* cited by examiner

*Primary Examiner* — Constantine Hannaher
(74) *Attorney, Agent, or Firm* — Dean D. Small; The Small Patent Law Group

(57) ABSTRACT

Methods and systems for positioning detectors for Nuclear Medicine (NM) imaging are provided. One system includes a gantry supporting one or more imaging detectors, wherein the gantry has a portion configured for movable operation. The system also includes a table on one side of the gantry configured to support a patient thereon, wherein the table is further configured to move within an opening of the gantry. The system further includes a patient support device movably positioned on an opposite side of the gantry from the table, wherein the patient support device is configured for movable operation.

22 Claims, 7 Drawing Sheets

METHODS AND SYSTEMS FOR POSITIONING DETECTORS FOR NUCLEAR MEDICINE IMAGING

BACKGROUND OF THE INVENTION

The subject matter disclosed herein relates generally to nuclear medicine (NM) imaging systems, and more particularly, to a method and system for positioning detectors for NM imaging.

NM imaging systems, for example, Single Photon Emission Computed Tomography (SPECT) imaging systems, use one or more imaging detectors to acquire image data, such as gamma ray or photon image data. The imaging detectors may be gamma cameras that acquire two-dimensional views of three-dimensional distributions of emitted radionuclides (from an injected radioisotope) from a patient being imaged.

When imaging a specific structure, organ or anatomy of the patient, such as the heart, liver or kidney, the patient must be positioned in relation to the detector or camera of the imaging system such that the structure to be imaged is within the field of view (FOV) of the imaging system, in particular, within the FOV of all of the imaging detectors. If the patient is not positioned correctly, the scan must be stopped and the patient repositioned. In other cases, the positioning problem may not be apparent during the acquisition, and thus acquired data may be reviewed and/or processed before it is found to be deficient. In some cases, incorrect positioning may case image artifacts such as truncation or distortion of the organ of interest. For example, when imaging a brain of a patient, the patient is typically positioned on a table of a SPECT imaging system. However, in this position it may be difficult to properly align the gantry to acquire images without artifacts. Thus, known systems and patient positioning within the systems are typically unable to preserve spatial and quantitative properties of the object to be reconstructed, for example, striata features in the brain, as well as the rest of the brain.

BRIEF DESCRIPTION OF THE INVENTION

In one embodiment, a medical imaging system is provided that includes a gantry supporting one or more imaging detectors, wherein the gantry has a portion configured for movable operation. The medical imaging system also includes a table on one side of the gantry configured to support a patient thereon, wherein the table is further configured to move within an opening of the gantry. The medical imaging system further includes a patient support device movably positioned on an opposite side of the gantry from the table, wherein the patient support device is configured for movable operation.

In another embodiment, a patient support device for medical imaging is provided. The patient support device includes a base defining a side and a patient platform supported by the base, wherein the patient platform is configured to maintain a patient in an upright position. The patient support device also includes a gantry engagement portion having a support panel extending from another side of the patient platform opposite the base. The gantry engagement portion includes an arm configured to engage the patient platform to an imaging system on a side of a gantry of the imaging system opposite to a table configured to support the patient in a supine position.

In a further embodiment, a method of imaging is provided. The method includes positioning a person in a patient support device on a side of a gantry of an imaging system opposite a table extending along an examination axis through an opening of the gantry, wherein the person is aligned perpendicular to the examination axis of the table. The method also includes adjusting one of a position of the patient support device or the gantry to align a head of a patient with at least one imaging detector supported by the gantry, wherein the head of the patient is aligned along a sagittal direction and having a left-right symmetry with respect to an axis of symmetry of the at least one imaging detector.

DETAILED DESCRIPTION OF THE INVENTION

Figure 1:
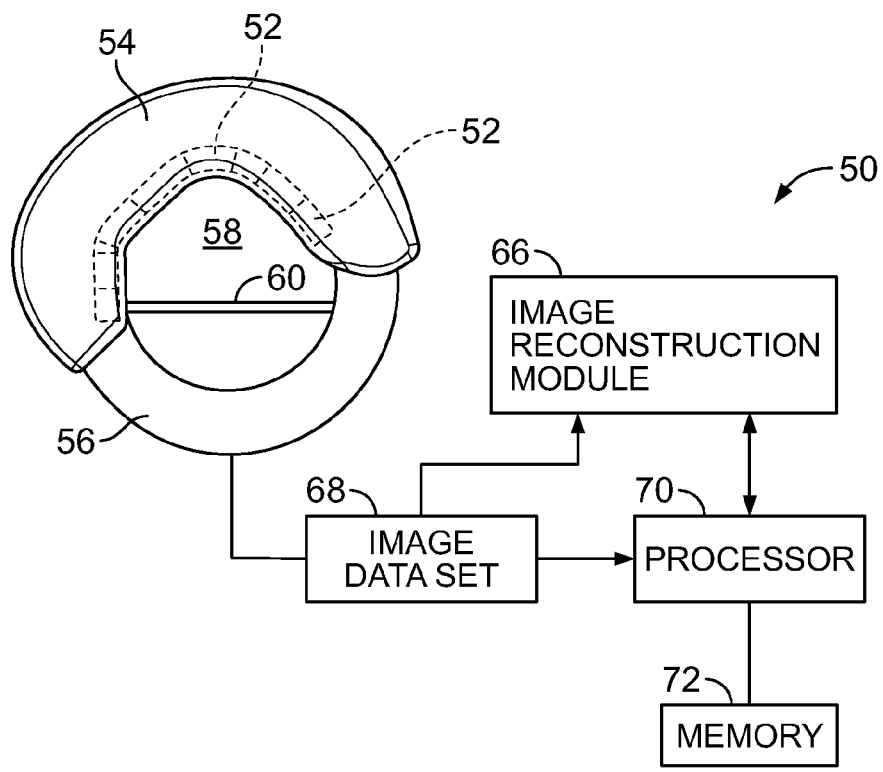
FIG. 1 is a simplified block diagram of an exemplary imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Described herein are exemplary imaging systems and methods that enable brain scanning, which may be performed with a limited field of view nuclear medicine (NM) camera. For example, various embodiments provide patient and gantry positioning of the NM imaging system, such as a Single Photon Emission Computed Tomography (SPECT) imaging system, to perform brain imaging. At least one technical effect of various embodiments is the acquisition of images with reduced or eliminated artifacts, as well as preservation of spatial and quantitative properties of the object to be reconstructed, such as the brain.

Various embodiments provide an arrangement for NM imaging wherein a brain of a subject or patient is aligned with an examination axis (Z-axis). For example, an axis of symmetry of the brain (left-right symmetry) is aligned with an axis of symmetry of imaging detectors (e.g., gamma cameras), which in various embodiments is a Z-axis of symmetry. Accordingly, the head of the patient is aligned with the camera geometry. However, the various embodiments may be used to perform NM imaging of other objects, such as other areas of interest within a patient.

In various embodiments, the brain of a patient is aligned with an axis of symmetry, for example, with the cortex of the brain aligned closest to an imaging detector surface within a field of view (FOV) of the imaging detectors.

The various embodiments are described herein as implemented in connection with a NM imaging system. However, it should be appreciated that although the various embodiments are described in connection with a SPECT imaging system having a particular configuration, the various embodiments may also be implemented in connection with other types of single or dual-modality imaging systems.

The imaging system 50 may be provided as shown in FIG. 1. The exemplary imaging system 50 includes one or more detectors 52 within or supported on a rotating portion 54 of a gantry 56 having a central opening 58 or bore therethrough. In one embodiment, the one or more detectors 52 are dedicated limited FOV gamma cameras, such as pinhole collimated gamma camera modules. For example, the imaging system 50 may include the detectors 52 in a configuration to perform cardiac NM imaging. The rotating portion 54 in some embodiments extends from the gantry 56 on an opposite side to a table 60 (e.g., a patient table). The rotating portion 54 in some embodiments includes a housing that encompasses about 180 degrees along the gantry 56. In various embodiments, the rotating portion 54 only rotates during an initial positioning to align the detectors 52 with a portion of the patient. Thereafter, the rotating portion 54 and the detectors 52 remain stationary during image acquisition. Thus, in some embodiments, the imaging system 50 is configured such that the detectors 52 are configured as limited FOV gamma cameras that remain stationary during the entire image acquisition process. Accordingly, in various embodiments, the detectors 52 do not rotate around the patient during imaging acquisition, but remain in the same position as provided during the initial positioning.

The opening 58 is configured to receive an object therein, such as a patient supported on the table 60, which may be a movable patient table allowing the table 60 to move into and out of the opening 58. The patient may be positioned on a table side of the gantry 56 for performing dedicated imaging for the imaging system 50, such as cardiac imaging with the patient supported in a supine position on the table 60. In accordance with the various embodiments, the imaging system 50 is also used to perform imaging of a different region of the patient than the dedicated portion (e.g., heart) of the patient, which may be referred to as the dedicated imaging operation of the system while the patient is on the table 60. In this non-dedicated imaging embodiment, the patient is imaged on an opposite side of the gantry 56 to the table 60 as described in more detail herein. For example, the patient may be provided in a generally seated orientation adjacent the gantry 56 and opposite the table side of the gantry 56. The patient is positioned and the gantry 56 controlled to align the axis of symmetry of the brain of the patient with the axis of symmetry of the detectors 52.

Figure 2:
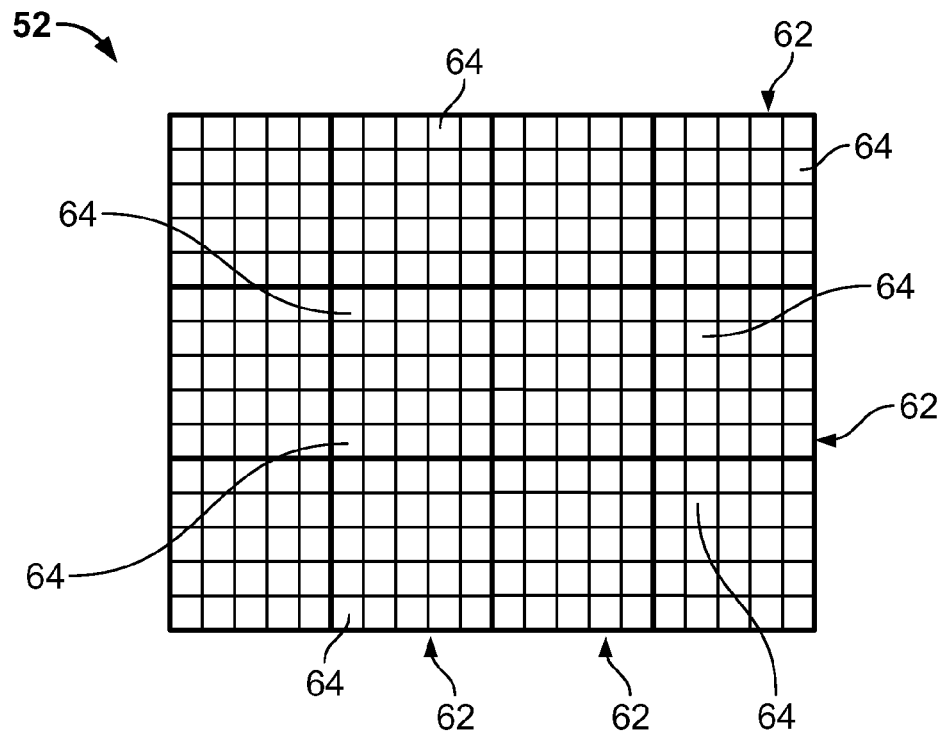
FIG. 2 is a diagram illustrating a pixelated imaging detector having a plurality of modules for use in the imaging system of FIG. 1.

It should be noted that the plurality of detectors 52 in some embodiments include (e.g., are fitted or installed with) pinhole collimators that are arranged about the object to be imaged, such as the patient or a region of interest (e.g., an organ) of the patient. The detectors 52 may be pixelated detectors configured to operate, for example, in an event counting mode. The pixelated detectors 52 may be configured to acquire SPECT image data. The detectors 52 may be solid-state detectors and/or may be formed from different materials, particularly semiconductor materials, such as cadmium zinc telluride (CdZnTe), often referred to as CZT, cadmium telluride (CdTe), and silicon (Si), among others. In some embodiments, a plurality of detector modules 62 are provided, each having a plurality of pixels 64 as shown in FIG. 2 and forming a detector 52.

The imaging system 50 also includes an image reconstruction module 66 that reconstructs images of a portion of the patient, for example, from an image data set 68. The image information from the image data set 68 corresponds to or is used to depict a portion of the patient being scanned (e.g., isotope concentration in a portion of the body of the patient providing functional information). The image reconstruction module 66 may be implemented in connection with or on a processor 70 (e.g., workstation) that is coupled to the imaging system 50. Optionally, the image reconstruction module 66 may be implemented as a module or device that is coupled to or installed in the processor 70. During operation, the output from the detectors 52, which may be the one or more image data sets 68, is transmitted to the image reconstruction module 66. The image reconstruction module 66 is configured to utilize the image data set 68, and in particular, event counts that are part of the image data set 68 to reconstruct an image of a portion of a patient. The image reconstruction module 62 may be implemented as a set of instructions or an algorithm installed on any computer that is coupled to or configured to receive the image data set 68, for example a workstation coupled to and controlling the operation of the imaging system 50.

Thus, for example, event count information, such as photon count information from a region of interest (e.g., brain or heart) of the patient is obtained from the modules 62 of the detectors 52. It should be noted that a pinhole may be associated, for example, with an array of 2×2 CZT modules. The pinholes are configured to be aimed at the primary region of interest of the patient (e.g., the dedicated organ for imaging), which in one embodiment, is the heart of the patient, injected with radiopharmaceutical and thus, each image depicts a different view of the isotope distribution in the patient. As described in more detail herein, the detectors 52 and the patient are also positioned to allow imaging of another region of interest, which in various embodiments, is the brain of the patient.

Thus, the image data set 68, which may include raw image data for a plurality of modules 62 of the detectors 52, may be reconstructed into a plurality of images, such as SPECT images of a heart or brain of the patient. It should be noted that the raw data, such as the image data sets 68 may be stored for a short term (e.g., during processing) or for a long term (e.g., for later offline retrieval) in a memory 72. The memory 72 may be any type of data storage device, which may also store databases of information. The memory 72 may be separate from or form part of the processor 70.

Figure 3:
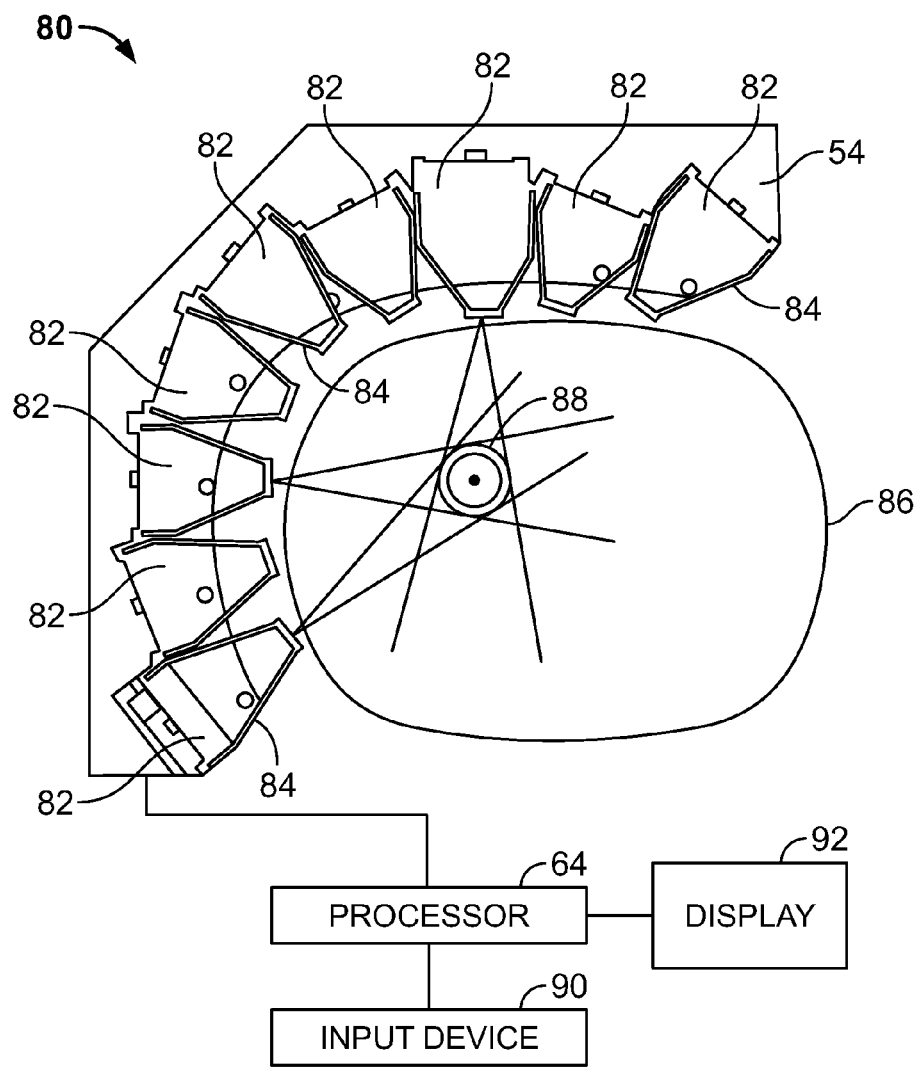
FIG. 3 is a diagram of an imaging portion of an imaging system in accordance with an embodiment.

FIG. 3 illustrates a simplified block schematic diagram of a portion of the imaging system 50 formed in accordance with various embodiments. The imaging system 50 includes an NM camera configured as a SPECT detector 80, which may form part of the rotating portion 54 (shown in FIG. 1). The SPECT detector 80 includes N detector modules 82, which may be embodied as the imaging detectors 52 of FIG. 1. In one embodiment, N=19. In some embodiments, the array of modules 82 is a multidimensional array wherein modules 82 are arranged in a plurality of rows (only one such row is seen in the cross-sectional view depicted in FIG. 3). It should be noted that the various embodiments are not limited to the NM imaging system 50 having a single detector 80 operable to perform SPECT imaging. For example, the NM imaging system 50 may include one or more additional detectors 80.

In one embodiment, the detector modules 82 are formed from pixelated detector elements that may operate, for example, in an event counting mode and may be configured to acquire SPECT image data. The detector modules 82 in the illustrated embodiment define a limited FOV gamma camera wherein pinhole collimation is provided by pinhole collimators 84 that may be coupled to the face of the detector modules 80. The collimators 84, in some embodiments, define a single or multi-pinhole collimator arrangement. As used herein, the term "pinhole camera" refers to the combination of a single detector module 82 and a corresponding collimator, if utilized. Accordingly, in the exemplary embodiment, the detector 80 is formed to include N pinhole cameras.

In the illustrated embodiment, the detector modules 82 are configured as pinhole cameras that are arranged and supported on a support structure, illustrated as the rotating portion 54 of the gantry 56 (shown in FIG. 1) and are provided in a generally curved or arcuate configuration. Thus, the detector 80 has a generally semi-arc shape or L-shaped arrangement similar to an L-mode of operation. The detector modules 82 may be arranged to provide, for example, organ specific imaging such that each of the detector modules 82 is fixed on the support structure and conforms to the shape of the patient 86. However, the detector modules 82 may be configured for different types of organ specific imaging or for general purpose imaging.

In the exemplary embodiment, the detector modules 82 are arranged on the support structure such that the FOV for each detector modules 82 is focused on the same region of interest (ROI) and remain in a fixed focused position during image acquisition, such that the rotating portion 54 and the detector modules 82 do not move during image acquisition. For example, as shown in FIG. 3, the detector modules 82 are each aligned to receive information from a single ROI 88. Thus the FOV for each respective detector module 82 may overlap to encompass the ROI 88, which in the illustrated embodiment is the dedicated imaging organ, which is the heart in some embodiments. As described in more detail herein, for brain imaging, the rotating portion 54 of the gantry 56 is moved such that the axis of symmetry of the brain is aligned with the axis of symmetry of the SPECT detector 80, and thereafter remains in a fixed position during image acquisition. Moreover, as described in more detail herein, different symmetry alignments may be provided and the various embodiments are not limited to alignment with the brain.

It should be noted that the imaging system 50 also includes an input device 90 that is configured to receive information from a user and transmit information to the processor 70. The imaging system 50 further includes a display device 92 for displaying various images as described in more detail below.

It also should be noted that although the various embodiments are described in connection with a limited FOV system, the various embodiments may be implemented with different imaging system configurations. For example, the various embodiments may be implemented in connection with systems having an unconventional SPECT imaging geometry of one having complex sensitivity-resolution properties.

Thus, the gantry 56 in various embodiments is configured to support one or more NM radiation detectors, which may be configured as CZT imaging modules, that are supported, for example, around approximately 180 degrees of the gantry 56. The patient table 60 also may include a bed slidingly coupled to a bed support system, which may be coupled directly to a floor or may be coupled to the gantry 56 through a base coupled to the gantry 56. The patient table 60 is configured to facilitate ingress and egress of a patient (not shown) into an examination position that is substantially aligned with the examination axis (Z-axis) of the gantry opening 58 to perform a first type of imaging. The patient table 60 may also configured to facilitate up and down motion of the patient 86. The operation and control of the imaging system 50 may be performed in any manner known in the art. It should be noted that the various embodiments may be implemented in connection with imaging systems that include stationary gantries or moving gantries.

Figure 4:
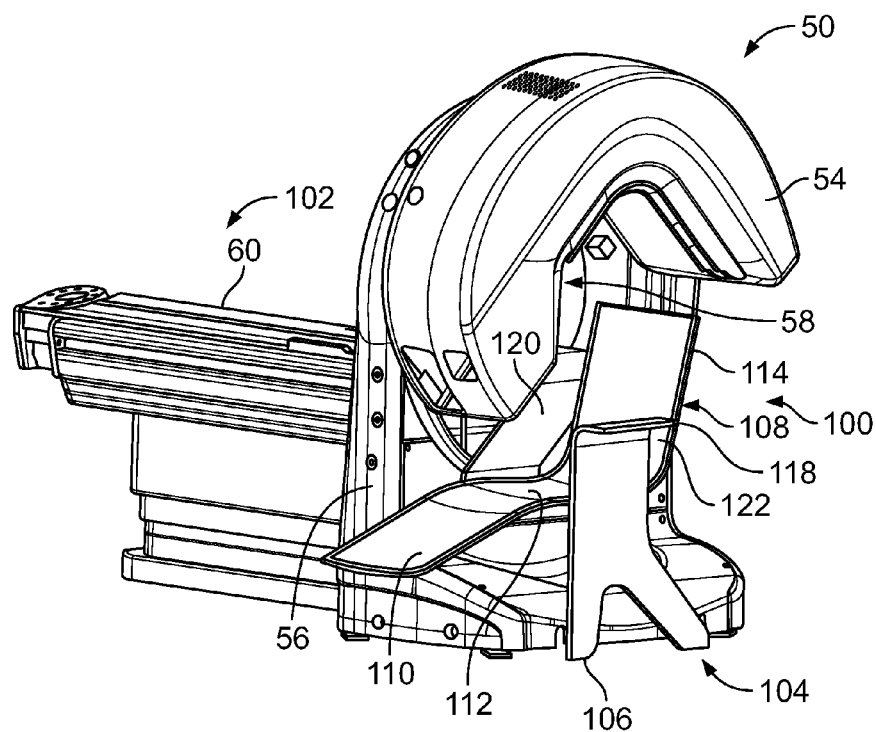
FIGS. 4 and 5 are perspective views of an imaging system illustrating a patient support device in accordance with an embodiment.
Figure 5:
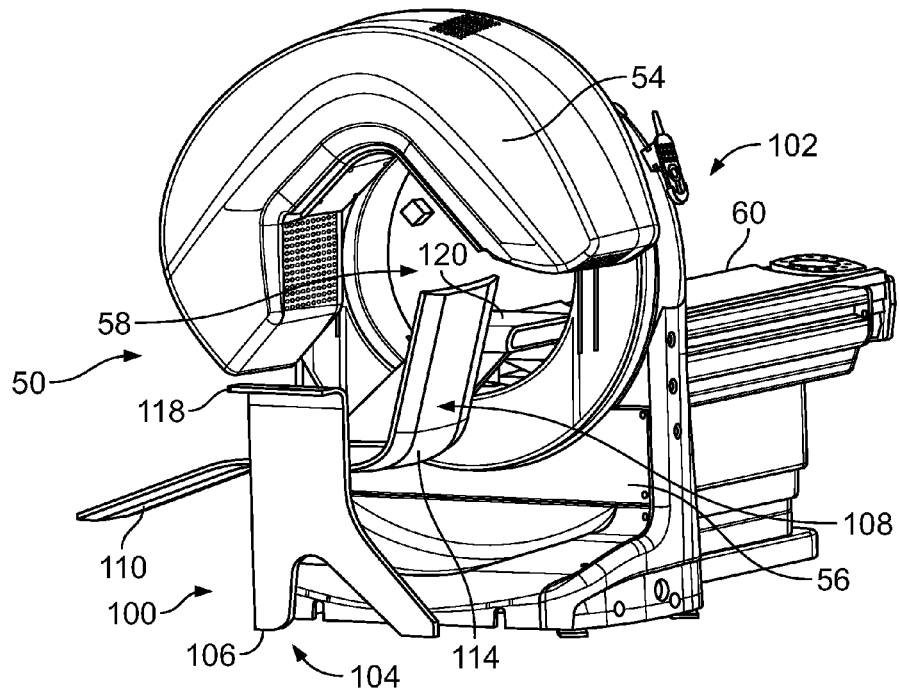
Figure 6:
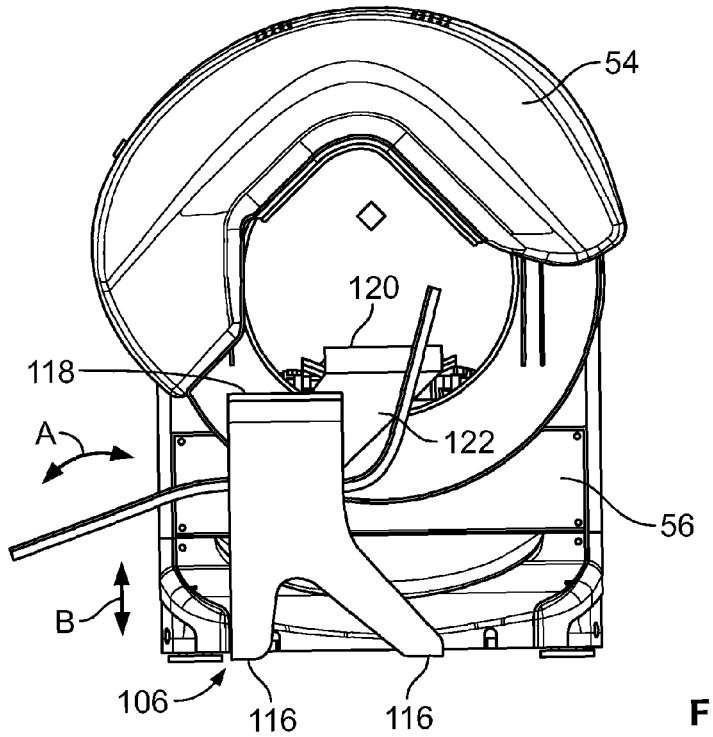
FIGS. 6 and 7 are elevation views of the imaging system of FIGS. 4 and 5.
Figure 7:
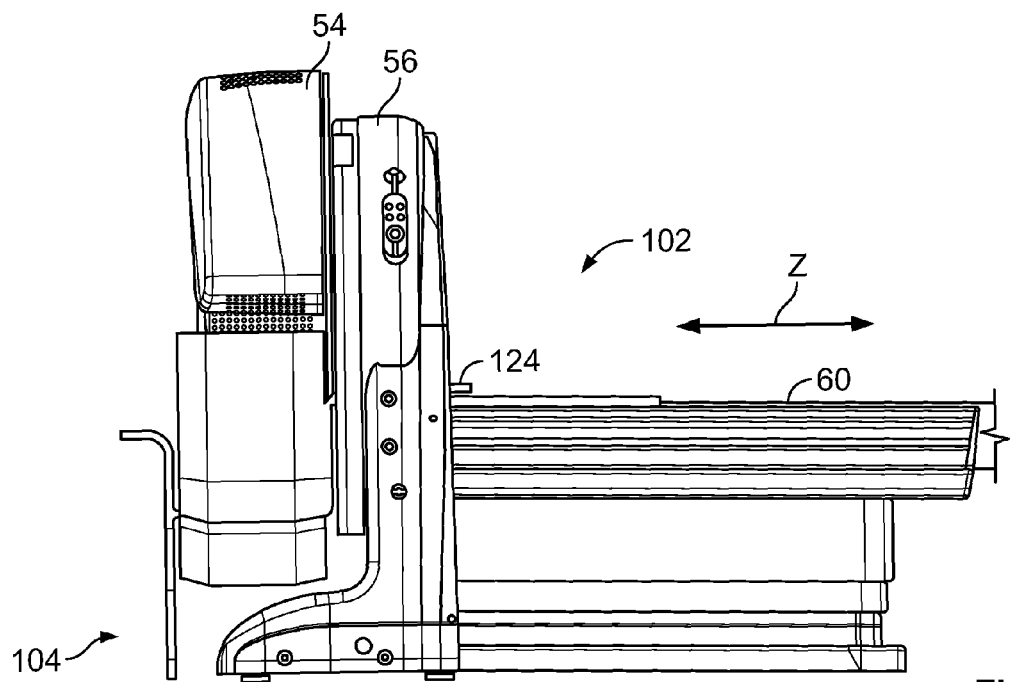

Various embodiments also allow for imaging another ROI of the patient 86, such as to perform a second type of imaging, thereby allowing different imaging applications. For example, in addition to cardiac imaging with the patient 86 positioned supine on the table 60, the imaging system 50 may be controlled for use is neurological applications, such as to image the brain of the patient 86 as shown in FIGS. 4 through 6. As can be seen, for performing the brain imaging, the patient 86 is imaged on an opposite side 100 of the gantry 56 from a table side 102. Thus, in operation, for cardiac imaging, the patient 86 is positioned on the table 60 and then the patient 86 moved (e.g., translated) into the opening 58 (which may include up/down or left-right movement of the table) to align the heart of the patient 86 with the imaging detectors 52 or detector modules 82 (shown in FIGS. 1 and 3). It should be noted that this alignment also may include movement of the rotating portion 54 of the gantry 56. Thus, for cardiac imaging the patient is positioned on the table side 102 and then moved into the opening 58. For brain imaging, the patient 86 is positioned on the opposite side 100 of the gantry 56 to the table side 102 and supported on a structure in a seated position.

In the illustrated embodiment, the patient 86 is supported by a patient support device, which in one embodiment is a patient chair 104. The patient chair 104 includes a base 106 with legs. The base 106 defines one side of the patient chair 104 and supports a patient platform 108 that allows the patient 86 to be maintained in a seated or generally upright position for brain imaging. The patient platform 108 includes a lower portion 110 for supporting legs of the patient 86, a middle portion 112 that supports the posterior of the patient 86 and an upper portion 114 that defines a chair back to support the upper portion of the patient 86 including the back of the patient 86. It should be noted that one of more of the lower, middle and upper portions 110, 112, 114 may be padded and/or include other coverings to increase patient comfort, as well as facilitate cleaning of the surface of these portions.

The patient platform may be moved, for example, tilted (left and right as viewed in FIG. 6) to raise or lower in a titling manner the upper and lower portions 110 and 114 as illustrated by the A arrow, such as rotated relative to the base 106. Thus, the patient 86 may be moved and positioned more upright or reclined. Additionally, in some embodiments, the patient platform 108 may be moved vertically upward and downward along the base 106 as illustrated by the B arrow. The base 106 extends generally vertically from legs 116 past the side of the patient platform 108 and defines an arm portion 118 for supporting an arm (e.g., left arm) of the patient 86.

The patient chair 104 also includes a gantry engagement portion 120 for engaging the patient chair 104 with the imaging system 50, in particular, to the gantry 56 within the opening 58. In the illustrated embodiment, the gantry engagement portion 120 includes a support panel 122 that extends from the middle portion 112 of the patient platform 108 upward and includes an arm 124 that abuttingly engages the gantry 56 within the opening 58 and is supported on a top of the table 60. It should be noted that the arm 124 may rest on the table 60 or may be removably secured to the table 60. It also should be noted that in one embodiment, as illustrated, the support panel 122 extends upward and generally inward from a right edge of the middle portion 112 and is curved at a height of the top of the table 60 (e.g., curved 90 degrees) such that the arm forms a generally horizontal platform at the height of the top of the table 60. The arm 124 extends a distance therefrom such that the planar portion of the arm 124 engages at least a portion of the table 60, such as extending through the opening 58 to the table side 102. However, it should be noted that the arm 124 may be longer or shorter as desired or needed.

In the illustrated embodiment, the arm 124, support panel 122 and middle portion 112 together form a generally "Z" shaped support member as viewed along the examination or Z-axis of the imaging system 50. In operation, the patient chair 104 may be moved into an engaged position as shown in FIGS. 4 through 6 to perform brain imaging of the patient 86 as described in more detail below. In this position, the patient 86 is supported such that one side of the patient 86 (e.g., the right side of the patient 86) is positioned adjacent or proximate to the gantry 56. However, the configuration and position of the patient chair 104 may be changed such that the opposite side of the patient 86 is positioned adjacent or proximate to the gantry 56. In various embodiments, the longitudinal axis of the patient chair 104 is aligned generally perpendicular to the gantry 56, for example, generally perpendicular to the table 60.

Figure 8:
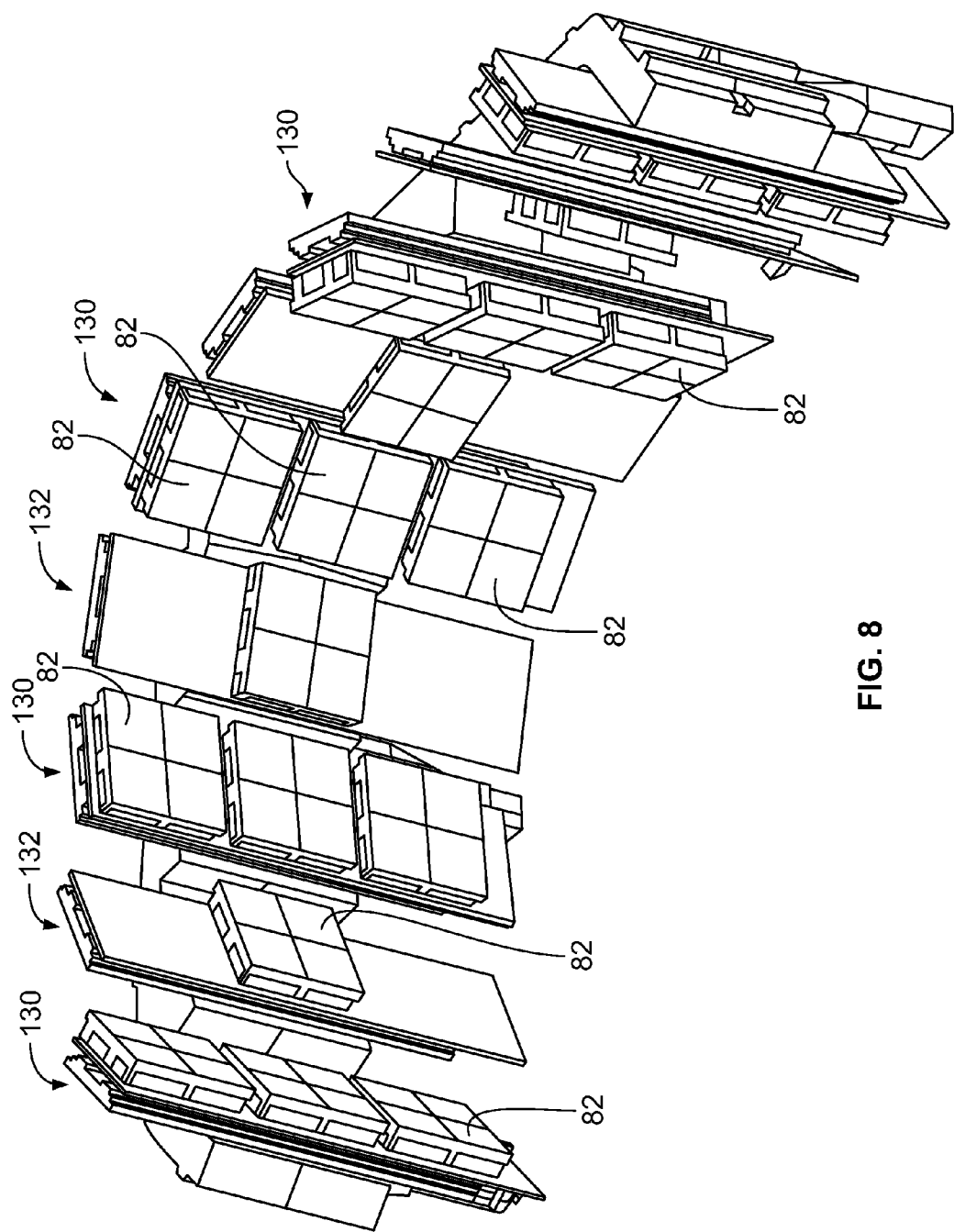
FIG. 8 is a diagram illustrating a detector arrangement in accordance with an embodiment.

The legs 116 of the patient chair 104 may include wheels or similar devices for moving the patient chair 104 when not in use, such as when the imaging system 50 is used to image the patient 86 supported on the table 60 (e.g., cardiac imaging). The patient chair 104 in various embodiments operates as a positioning accessory to position the patient 86 for brain imaging. It should be noted that the rotating portion 54 also may be configured to move laterally as well as rotationally, such that the imaging detectors 52 or detector modules 82 (shown in FIGS. 1 and 3) may be positioned for brain imaging as described below. For example, in one embodiment, multiple rows of imaging detectors 52 or detector modules 82 are provided as shown in FIG. 8. The imaging detectors 52 or detector modules 82 may be arranged as triplets 130 or as individual modules 132. In the illustrated embodiment, an individual module 132 is positioned between each triplet 130. However, other arrangements are contemplated, and the module configuration of FIG. 8 is shown merely for example.

Figure 9:
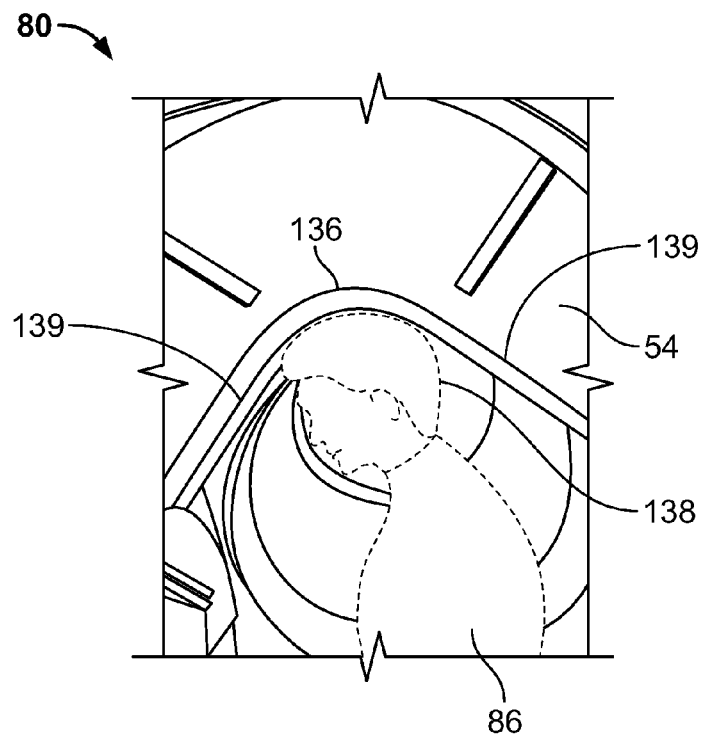
FIG. 9 is a diagram illustrating an axis of symmetry alignment in accordance with various embodiments.

In various embodiments, the patient 86 is positioned in a sitting or seated position as shown in FIG. 9 supported on the patient chair 104 (shown in FIGS. 4 through 7). The gantry 56, and in particular, the rotating portion 54 is moved such that a curved portion 136 is aligned with a top of the patient's head 138 with the imaging detectors 52 or detector modules 82 extending generally from a front (e.g., forehead) of the head 138 of the patient 86 to a back (e.g., backside) of the head 138 of the patient 86. For example, the rotating portion 54 is rotated (and optionally translated) to position the imaging detectors 52 or detector modules 82 on top of the patient's skull as shown in FIG. 9. The curved portion 136 is moved into close proximity to the patient's head 138. It should be noted that one or more position sensitive device (PSDs) may be provided, such as on the flat portions 139 to identify when the rotating portion 54 is in close proximity to the patient's head 138 and in an imaging position (e.g., with the imaging detectors 52 or detector modules 82 positioned a predetermined distance from the patient's head 138). In one embodiment, the rotating portion 54 is initially in a home position and then rotated a predetermined amount (e.g., 210 degrees from the home position). Thereafter, additional movements may be made, such as controlled by an operator.

The patient's head 138 is positioned between ends of the rotating portion 54 of the gantry 56 in various embodiments. For example, the patient chair 104 is sized and shaped to allow the rotating portion 54 to rotate about the patient 86 while the patient 86 is supported in the patient chair 104. In particular, in various embodiments, the rotating portion 54 rotates along a sagittal plane of the patient 86 such as to align the rotating portion 54 with the patient's head 138 therebetween during an initial positioning process. Thus, in various embodiments, the rotating portion 54 rotates from a front to back, and vice versa, of the patient's head 138. It should be noted that when the patient 86 is positioned on the table 60 the rotating portion 54 rotates along an axial plane transverse to the head-toe direction of the patient 86.

It also should be noted that the PSDs or other devices may be used to identify if the rotating portion 54 contacts the patient's head 138, in which case, movement may be halted and optionally reversed.

Figure 10:
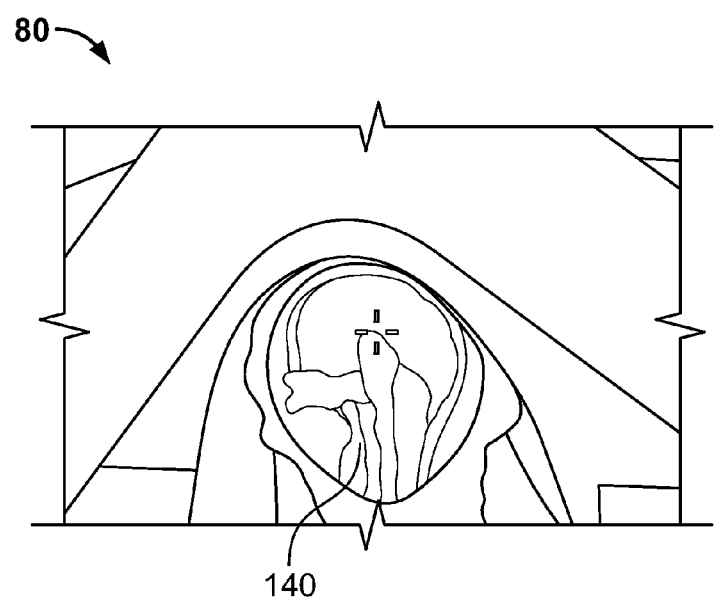
FIG. 10 is another diagram illustrating an axis of symmetry alignment in accordance with various embodiments.

As can be seen in FIG. 9, the imaging detectors 52 or detector modules 82 are positioned such that the brain of the patient 86 is positioned symmetrically with the camera axis symmetry. For example, the left-right symmetry of the brain is aligned with the axis symmetry of the imaging detectors 52 or detector modules 82. FIG. 10 shows the brain 140 of the patient 86 for illustration. As can be seen, the brain 140 is oriented such that the axis of symmetry of the brain is aligned with the camera axis of symmetry, namely the axis of symmetry of the imaging detectors 52 or detector modules 82 with the brain 140 symmetrically aligned within the FOV of the imaging detectors 52 or detector modules 82. The cortex of the brain 140 is aligned adjacent the imaging detectors 52 or detector modules 82 with the patient 86 seated and aligned with the gantry 56. In various embodiments, the imaging detectors remain in the fixed position during the entire image acquisition process for either the primary region of interest or another region of interest.

It should be noted that the patient chair 104 is one example of a patient support structure that may be used to image the patient 86 on the opposite side 100 of the gantry 56 than the table side 102. For example, any type of patient support device or structure may be used in some embodiments to maintain the position and/or orientation of the patient 86 relative to the imaging detectors 52 or detector modules 82. In some embodiments, the patient chair 104 or other device may be self-supporting such that no engagement is provided with the imaging system 50. In still other embodiments, the patient chair 104 may abut or engage different portions of the imaging system 50, for example, different portions of the gantry 56, which may include secure engagement (such as using a fastening mechanism).

Figure 11:
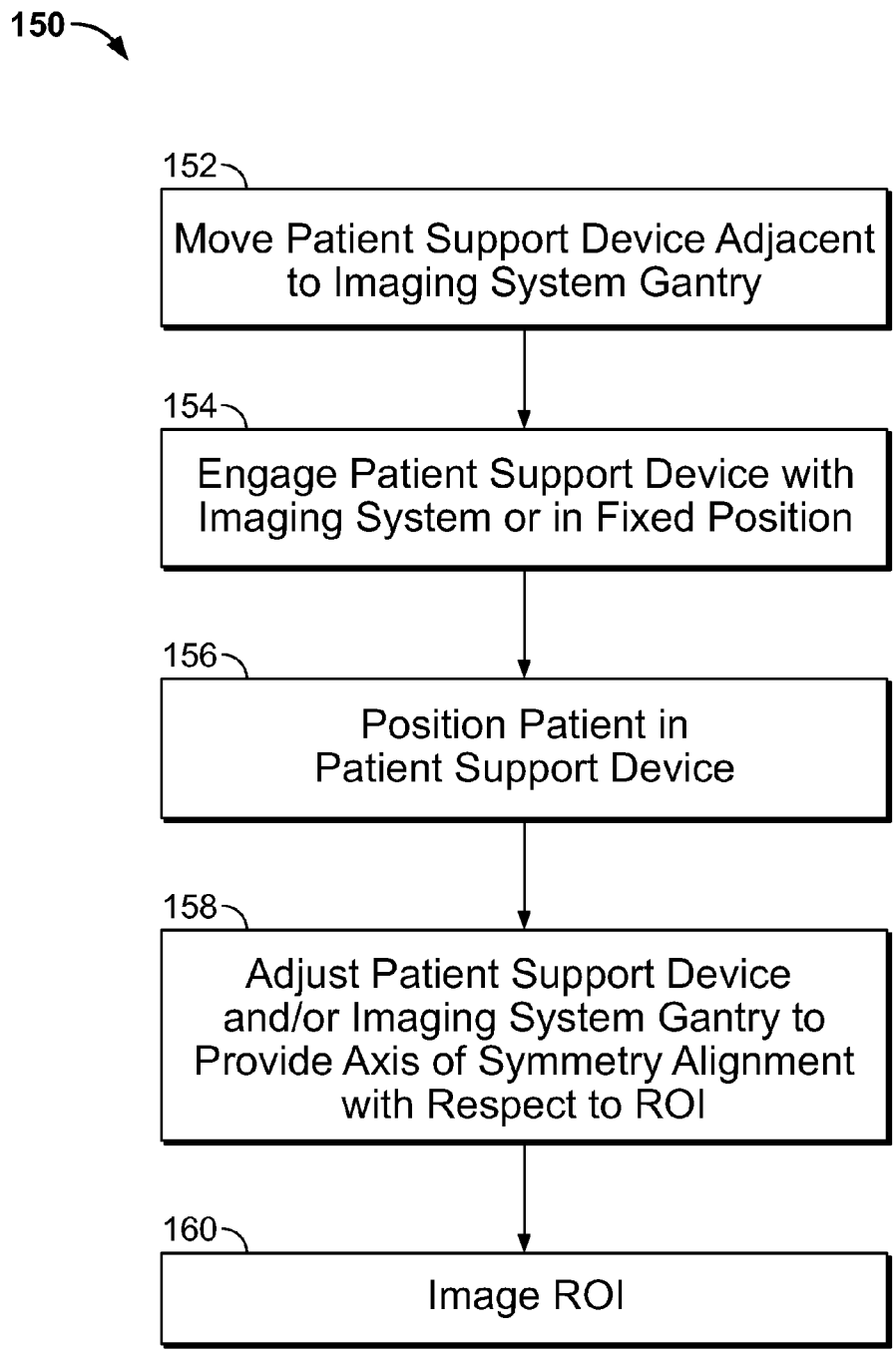
FIG. 11 is a flowchart of a method for imaging in accordance with various embodiments.

Various embodiments also provide a method 150 as shown in FIG. 11 for imaging. The method 150 includes moving a patient support device (e.g., the patient chair 104) adjacent to an imaging system at 152. For example, the patient support device may be moved adjacent to a gantry of a SPECT imaging side on an opposite side to the patient table. It should be noted that the patient support device may be stored in the imaging room or another room, such as when not in use. With the patient support device adjacent to the imaging system, which may be in abutting alignment with a portion of the imaging system, the patient support device is engaged with the imaging system or in a fixed position at 154. For example, in one embodiment, the patient support device includes an engagement portion for securing to or being supported on (as described in more detail herein) the imaging system to maintain the position of the patient support device. In another embodiment, the patient support device is self-supporting and does not engage the imaging system, for example, includes locking devices (e.g., locking wheels) that maintains the position and orientation of the patient support device with respect to the imaging system.

A patient is then positioned in the patient support device at 156. For example, a patient is supported on the patient support device is a seated orientation. Thereafter, the patient support device and/or the imaging system gantry is adjusted at 158 to provide an axis of symmetry alignment between imaging detectors and/or detector modules (supported by the gantry of the imaging system) and a ROI of the patient. For example, in one embodiment, the patient support device is moved (e.g., translated, raised, lowered and/or titled) and/or the gantry is moved (e.g., rotated and/or translated) such that the left-right brain axis of symmetry is aligned with the detector axis of symmetry prior to image acquisition. In one embodiment, this axis of symmetry alignment includes the patient supported in a seated or generally upright position with his or her side adjacent the imaging system gantry. It should be noted that the movement of the patient support device and the various components of the imaging system may be manually performed by an operator and/or mechanically performed (e.g., using one or more motors and drives), which may include automatic or semi-automatic operation.

With the imaging detectors or detector modules positioned to provide the axis of symmetry alignment and in close proximity to the patient's head, for example, as described herein, the ROI, which in this example is the patient's brain, is imaged at 160. For example, in one embodiment, the patient is injected with a radiopharmaceutical either before or after being positioned in the patient support device, which may be before or after the axis of symmetry alignment is performed. A SPECT scan of the patient's brain then may be performed using the imaging system. The imaging may include, for example, using image reconstruction techniques, for example, dedicated image reconstruction techniques incorporating relevant knowledge of the system and/or object properties to achieve certain diagnostic properties.

It should be noted that the various embodiments may be used to image other ROIs of the patient by aligning the ROIs with the imaging detectors 52 or detector modules 82. For example, the axis of symmetry of an object or ROI within the patient is aligned with the axis of symmetry of the imaging detectors 52 or detector modules 82. The ROI may be, for example, different regions within the patient instead of the brain, such as the parathyroid. However, the various embodiments may be used to image other regions of the patient.

In general, various embodiments allow alignment of an ROI, such as particular features of interest, with the imaging detectors 52 or detector modules 82 to improve or optimize sensitivity and resolution of the system for the ROI. For example, different symmetrical alignments may be performed (e.g., positioning of the imaging detectors 52 or detector modules 82) that provides improved or optimized imaging properties of the system for the particular object. Thus, in some embodiments, the imaging detectors 52 or detector modules 82 are aligned to increase the sensitivity and/or resolution properties for imaging the object of interest, which may include, for example, aligning an axis of symmetry of the object with an axis of symmetry of the imaging detectors 52 or detector modules 82.

Various embodiments described herein provide methods and/or systems for using an imaging system, for example, a dedicated SPECT imaging system to also image other regions of interest of the patient, such as the brain instead of the heart (for a dedicated cardiac SPECT scanner).

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A medical imaging system comprising:
   a gantry supporting one or more imaging detectors, the gantry having a portion configured for movable operation;
   a table on one side of the gantry configured to support a patient thereon, the table further configured to move within an opening of the gantry; and
   a patient support device movably positioned on an opposite side of the gantry from the table, the patient support device configured for movable operation, the patient support device comprising a gantry engagement portion that secures the patient support device to the gantry.

2. The medical imaging system of claim 1, wherein the movable portion of the gantry and the table are together configured to align an axis of symmetry of a region of interest of an object with an axis of symmetry of the one or more imaging detectors.

3. The medical imaging system of claim 2, wherein the region of interest is a brain of a person.

4. The medical imaging system of claim 1, wherein the patient support device is configured to support a person is an upright position.

5. The medical imaging system of claim 1, wherein a longitudinal axis of the patient support device is aligned perpendicular to the gantry.

6. The medical imaging system of claim 1, wherein the patient support device comprises a patient chair configured to tilt to raise or lower a head of a patient relative to the gantry.

7. The medical imaging system of claim 1, wherein the patient support device comprises a patient chair having a support arm that engages within an opening of the gantry.

8. The medical imaging system of claim 7, wherein the support arm engages a top surface of the table.

9. The medical imaging system of claim 1, wherein the patient support device is configured to support a patient in a position with a side of the patient adjacent the gantry.

10. The medical imaging system of claim 1, wherein the gantry is configured to rotate, with the patient support device secured to the gantry via the patient engagement mechanism, such that the at least one imaging detector extends from a front of a head of a patient in the patient support device to a back of the head of the patient.

11. The medical imaging system of claim 1, wherein the patient support device comprises a patient chair that includes a lower portion configured to support legs of a patient, a middle portion to support a posterior of the patient, and a top portion to support a back of the patient.

12. The medical imaging system of claim 1, wherein the patient support device comprises a patient chair configured to support a head of a patient between ends of a rotating portion of the gantry that includes the at least one imaging detector.

13. The medical imaging system of claim 1, wherein the at least one imaging detector comprises a gamma camera configured to acquire Single Photon Emission Computed Tomography (SPECT) data.

14. The medical imaging system of claim 13, wherein the gamma camera is a dedicated cardiac gamma camera.

15. The medical imaging system of claim 1, wherein the table is configured to support the patient for cardiac imaging and the patient support device is configured to support the patient for brain imaging.

16. The medical imaging system of claim 1, wherein the one or more imaging detectors comprises a plurality of nuclear medicine (NM) imaging detectors positioned in a fixed relationship to one another in at least one of a semi-arc shape or "L" shape and aligned to receive information from a single region of interest (ROI) when used to image a patient in the patient support device, the NM imaging detectors remaining stationary during imaging.

17. A patient support device for medical imaging, the patient support device comprising:
   a base defining a side;
   a patient platform supported by the base, the patient platform configured to maintain a patient in an upright position; and
   a gantry engagement portion having a support panel extending from another side of the patient platform opposite the base, the gantry engagement portion including an arm configured to engage the patient platform to an imaging system on a side of a gantry of the imaging system opposite to a table configured to support the patient in a supine position.

18. The patient support device of claim 17, wherein a longitudinal axis of the patient platform is configured to align perpendicular to the table.

19. The patient support device of claim 17, wherein the patient platform defines a chair portion configured to support the patient in a seated position.

20. The patient support device of claim 17, wherein the patient platform is tiltable relative to the base.

21. A method of imaging, the method comprising:
positioning a person in a patient support device on a side of a gantry of an imaging system opposite a table extending along an examination axis through an opening of the gantry, the patient support device secured to the gantry via a gantry engagement portion, the person aligned perpendicular to the examination axis of the table; and
adjusting one of a position of the patient support device or the gantry to align a head of a patient with at least one imaging detector supported by the gantry, the head of the patient aligned along a sagittal direction and having a left-right symmetry with respect to an axis of symmetry of the at least one imaging detector.

22. The method of claim 21, further comprising rotating a rotating portion of the gantry to position a detector portion of the gantry to be aligned with a top of the head of the person positioned in the patient support device with detectors of the detector portion extending from a front of the head of the person to a back of the head of the person, wherein the detector portion is positioned on top of and in close proximity to the head of the person.

* * * * *